(12) United States Patent
Belleville

(10) Patent No.: US 11,786,130 B2
(45) Date of Patent: *Oct. 17, 2023

(54) GUIDEWIRE WITH INTERNAL PRESSURE SENSOR

(71) Applicant: OPSENS INC., Quebec (CA)

(72) Inventor: Claude Belleville, Ville de Quebec (CA)

(73) Assignee: Opsens Inc., Quebec (CA)

( * ) Notice: Subject to any disclaimer, the term of this patent is extended or adjusted under 35 U.S.C. 154(b) by 370 days.

This patent is subject to a terminal disclaimer.

(21) Appl. No.: 16/923,762

(22) Filed: Jul. 8, 2020

(65) Prior Publication Data

US 2020/0329972 A1    Oct. 22, 2020

Related U.S. Application Data

(63) Continuation of application No. 16/128,957, filed on Sep. 12, 2018, now Pat. No. 10,750,949, which is a
(Continued)

(51) Int. Cl.
*A61B 5/00* (2006.01)
*A61M 25/09* (2006.01)
(Continued)

(52) U.S. Cl.
CPC ........ *A61B 5/0084* (2013.01); *A61B 5/02154* (2013.01); *A61B 5/6851* (2013.01);
(Continued)

(58) Field of Classification Search
CPC . A61B 5/0084; A61B 5/02154; A61B 5/6851; A61M 2025/0002;
(Continued)

(56) References Cited

U.S. PATENT DOCUMENTS

| 3,273,447 A | 9/1966 | Frank |
| 3,590,638 A | 7/1971 | Anastasia |

(Continued)

FOREIGN PATENT DOCUMENTS

| DE | 202014100938 | 3/2014 |
| EP | 0 235 992 | 9/1987 |

(Continued)

OTHER PUBLICATIONS

Tohyama et al.. "A Fiber-Optic Silicon Pressure Sensor for Ultra-Thin Catheters", The 8th International Conference on Solid-State Sensors and Actuators, and Eurosensors IX, Stockholm, Sweden, Jun. 25-29, 1995 (Jun. 25, 1995), p. 596, right col., line 1 to p. 598, left col., line 8, Fig. 3, 4.

(Continued)

*Primary Examiner* — Eric J Messersmith
(74) *Attorney, Agent, or Firm* — BENOIT & COTE INC.; Charles-Andre Caron

(57) ABSTRACT

There is described a pressure guidewire. It comprises a sensor housing and a sensor assembly embedded in the sensor housing and comprising a pressure sensor. There is a band to support the pressure sensor assembly, the band being embedded inside the sensor housing and fixed to the pressure sensor assembly for holding the pressure sensor inside the sensor housing.

20 Claims, 8 Drawing Sheets

Related U.S. Application Data continuation of application No. 15/918,677, filed on Mar. 12, 2018, now Pat. No. 10,154,787, which is a continuation of application No. 14/138,392, filed on Dec. 23, 2013, now Pat. No. 9,968,260, which is a continuation of application No. 14/030,425, filed on Sep. 18, 2013, now abandoned, which is a continuation of application No. 13/389,319, filed as application No. PCT/CA2011/001257 on Nov. 9, 2011, now abandoned.

(60) Provisional application No. 61/411,722, filed on Nov. 9, 2010.

(51) Int. Cl.
  *A61B 5/0215* (2006.01)
  *A61M 25/00* (2006.01)

(52) U.S. Cl.
  CPC ..... *A61M 25/09* (2013.01); *A61M 2025/0002* (2013.01); *A61M 2025/09083* (2013.01); *A61M 2025/09108* (2013.01); *A61M 2025/09133* (2013.01); *A61M 2025/09166* (2013.01); *A61M 2025/09183* (2013.01); *A61M 2205/3327* (2013.01)

(58) Field of Classification Search
  CPC ......... A61M 2025/09083; A61M 2025/09108; A61M 2025/09133; A61M 2025/09166; A61M 2025/09183; A61M 2205/3327; A61M 25/09
  See application file for complete search history.

(56) References Cited

U.S. PATENT DOCUMENTS

| | | |
|---|---|---|
| 3,963,323 A | 6/1976 | Arnold |
| 4,678,904 A | 7/1987 | Saaski et al. |
| 4,682,500 A | 7/1987 | Uda |
| 4,726,232 A | 2/1988 | Koneval |
| 4,771,782 A | 9/1988 | Millar |
| 4,953,553 A | 9/1990 | Termulis |
| 4,983,824 A | 1/1991 | Saaski et al. |
| 5,085,223 A | 2/1992 | Tenerz et al. |
| 5,106,455 A | 4/1992 | Jacobsen et al. |
| 5,125,058 A | 6/1992 | Tenerz et al. |
| 5,128,537 A | 7/1992 | Halg |
| 5,178,159 A | 1/1993 | Christian |
| 5,187,761 A | 2/1993 | Mehadji et al. |
| 5,226,423 A | 7/1993 | Tenerz et al. |
| 5,238,004 A | 8/1993 | Sahatjian et al. |
| 5,280,786 A | 1/1994 | Wlodarczyk et al. |
| 5,313,957 A | 5/1994 | Little |
| 5,313,967 A | 5/1994 | Lieber et al. |
| 5,315,110 A | 5/1994 | Smith |
| 5,385,053 A | 1/1995 | Wlodarczyk et al. |
| 5,392,117 A | 2/1995 | Belleville et al. |
| 5,421,195 A | 6/1995 | Wlodarczyk |
| 5,422,969 A | 6/1995 | Eno |
| 5,427,114 A | 6/1995 | Colliver et al. |
| 5,429,617 A * | 7/1995 | Hammersmark . A61M 25/0108 604/117 |
| 5,438,873 A | 8/1995 | Wlodarczyk et al. |
| 5,573,520 A | 11/1996 | Schwartz et al. |
| 5,601,087 A | 2/1997 | Gunderson et al. |
| 5,633,963 A | 5/1997 | Rickenbach et al. |
| 5,755,668 A | 5/1998 | Itoigawa et al. |
| 5,772,609 A | 6/1998 | Nguyen et al. |
| 5,797,856 A | 8/1998 | Frisbie et al. |
| 5,872,879 A | 2/1999 | Hamm |
| 5,902,248 A | 5/1999 | Millar et al. |
| 5,938,624 A | 8/1999 | Akerfeldt et al. |
| 5,949,929 A | 9/1999 | Hamm |
| 5,964,714 A | 10/1999 | Lafontaine |
| 6,106,486 A | 8/2000 | Tenerz et al. |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,193,669 B1 | 2/2001 | Degany et al. |
| 6,196,980 B1 | 3/2001 | Akerfeldt et al. |
| 6,210,339 B1 | 4/2001 | Kiepen et al. |
| 6,248,083 B1 | 6/2001 | Smith et al. |
| 6,265,792 B1 | 7/2001 | Granchukoff |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,445,939 B1 | 9/2002 | Swanson et al. |
| 6,508,803 B1 | 1/2003 | Horikawa et al. |
| 6,565,514 B2 | 5/2003 | Svanerudh et al. |
| 6,579,246 B2 | 6/2003 | Jacobsen et al. |
| 6,585,660 B2 | 7/2003 | Dorando et al. |
| 6,602,427 B1 | 8/2003 | Tu |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,823,738 B1 | 11/2004 | Wlodarczyk et al. |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,976,965 B2 | 12/2005 | Corl et al. |
| 6,993,974 B2 | 2/2006 | Tenerz et al. |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,173,713 B2 | 2/2007 | Xu et al. |
| 7,187,453 B2 | 3/2007 | Belleville |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,717,624 B2 | 5/2010 | Carlin et al. |
| 7,724,148 B2 | 5/2010 | Samuelsson et al. |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huennekens et al. |
| 7,946,997 B2 | 5/2011 | Hubinette |
| 8,029,447 B2 | 10/2011 | Kanz et al. |
| 8,142,363 B1 | 3/2012 | Eigler et al. |
| 8,149,647 B2 | 4/2012 | Borgen et al. |
| 8,149,648 B2 | 4/2012 | Daigle |
| 8,174,395 B2 | 5/2012 | Samuelsson et al. |
| 8,216,151 B2 | 7/2012 | Smith |
| 8,298,156 B2 | 10/2012 | Manstrom et al. |
| 8,343,076 B2 | 1/2013 | Sela |
| 8,393,802 B2 | 3/2013 | Stanley |
| 8,461,997 B2 | 6/2013 | Samuelsson et al. |
| 8,485,985 B2 | 7/2013 | Manstrom et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,752,435 B2 | 6/2014 | Belleville et al. |
| 8,936,401 B2 | 1/2015 | Belleville et al. |
| 8,998,823 B2 | 4/2015 | Manstrom et al. |
| 9,052,466 B2 | 6/2015 | Belleville et al. |
| 9,256,035 B2 | 2/2016 | Park et al. |
| 9,405,075 B2 | 8/2016 | Belleville et al. |
| 9,405,078 B2 | 8/2016 | Belleville et al. |

(56) References Cited

U.S. PATENT DOCUMENTS

| | | |
|---|---|---|
| 9,782,129 B2 | 10/2017 | Radman |
| 9,878,142 B2 | 1/2018 | Burkett |
| 9,895,108 B2 | 2/2018 | Burkett et al. |
| 9,901,260 B2 | 2/2018 | Manstrom et al. |
| 9,924,903 B2 | 3/2018 | Burkett |
| 9,943,235 B2 | 4/2018 | Burkett |
| 9,949,646 B2 | 4/2018 | Belleville |
| 9,955,878 B2 | 5/2018 | Burkett |
| 9,968,260 B2 | 5/2018 | Belleville |
| 9,974,446 B2 | 5/2018 | Burkett |
| 10,028,666 B2 | 7/2018 | Gregorich |
| 10,154,787 B2 | 12/2018 | Belleville |
| 2002/0003917 A1 | 1/2002 | Sherrer et al. |
| 2002/0013540 A1 | 1/2002 | Jacobsen et al. |
| 2002/0072680 A1 | 6/2002 | Schock et al. |
| 2002/0122635 A1 | 9/2002 | Rief et al. |
| 2002/0159711 A1 | 10/2002 | Lutzen et al. |
| 2002/0183597 A1 | 12/2002 | Kaufman et al. |
| 2003/0009095 A1 | 1/2003 | Skarda |
| 2003/0044124 A1 | 3/2003 | Saitoh |
| 2003/0069522 A1 | 4/2003 | Jacobsen et al. |
| 2003/0100838 A1 | 5/2003 | Ehr et al. |
| 2004/0073141 A1 | 4/2004 | Hartley et al. |
| 2004/0116816 A1 | 6/2004 | Tenerz et al. |
| 2004/0181174 A2 | 9/2004 | Davis et al. |
| 2004/0237659 A1 | 12/2004 | Mattmann |
| 2004/0244502 A1 | 12/2004 | Youngner et al. |
| 2005/0062979 A1 | 3/2005 | Zhu et al. |
| 2005/0183507 A1 | 8/2005 | Bailey et al. |
| 2005/0255317 A1 | 11/2005 | Bavaro et al. |
| 2005/0267444 A1 | 12/2005 | Griffin et al. |
| 2005/0268725 A1 | 12/2005 | Tulkki |
| 2006/0122537 A1 | 6/2006 | Reynolds et al. |
| 2006/0189896 A1 | 8/2006 | Davis et al. |
| 2008/0269641 A1 | 10/2008 | O'Shaughnessy et al. |
| 2008/0312671 A1 | 12/2008 | Riles et al. |
| 2009/0036832 A1 | 2/2009 | Skujins et al. |
| 2009/0082678 A1 | 3/2009 | Smith |
| 2009/0192412 A1 | 7/2009 | Sela et al. |
| 2010/0145308 A1 | 6/2010 | Layman et al. |
| 2010/0234698 A1* | 9/2010 | Manstrom ........ A61B 5/02158 600/478 |
| 2010/0241008 A1* | 9/2010 | Belleville ............ A61B 5/0215 600/478 |
| 2010/0318000 A1 | 12/2010 | Von Malmborg et al. |
| 2011/0071407 A1 | 3/2011 | Hubinette et al. |
| 2011/0178413 A1* | 7/2011 | Schmitt ................ A61B 5/0215 600/478 |
| 2011/0186294 A1 | 8/2011 | Narvaez et al. |
| 2011/0319773 A1 | 12/2011 | Kanz et al. |
| 2012/0265102 A1 | 10/2012 | Leo et al. |
| 2013/0296718 A1 | 11/2013 | Ranganathan et al. |
| 2013/0317372 A1 | 11/2013 | Eberle et al. |
| 2014/0005558 A1 | 1/2014 | Gregorich |
| 2014/0058275 A1 | 2/2014 | Gregorich et al. |
| 2014/0081244 A1 | 3/2014 | Voeller et al. |
| 2014/0107624 A1 | 4/2014 | Belleville |
| 2014/0121475 A1 | 5/2014 | Alpert et al. |
| 2014/0350414 A1 | 11/2014 | McGowan et al. |
| 2015/0032011 A1 | 1/2015 | McGowan et al. |
| 2015/0301288 A1 | 10/2015 | Thornton, Jr. |
| 2017/0082514 A1 | 3/2017 | Duplain et al. |
| 2018/0008153 A1 | 1/2018 | Burkett |
| 2018/0020929 A1 | 1/2018 | Gregorich |
| 2018/0103854 A1 | 4/2018 | Manstrom et al. |
| 2018/0214082 A1 | 8/2018 | Burkett et al. |
| 2019/0029523 A1 | 1/2019 | Belleville |

FOREIGN PATENT DOCUMENTS

| | | |
|---|---|---|
| EP | 0 313 836 | 5/1989 |
| EP | 0 738 495 | 10/1996 |
| EP | 0 879 615 | 11/1998 |
| EP | 0 879 617 | 11/1998 |
| EP | 1 479 407 | 11/2004 |
| EP | 0 907 335 | 9/2006 |
| EP | 2 085 108 | 8/2009 |
| EP | 1 733 198 | 1/2010 |
| EP | 3 174 455 | 6/2017 |
| GB | 2 038 016 | 10/1982 |
| JP | 2007-296354 | 10/2007 |
| JP | 2010-201027 | 3/2015 |
| SU | 746128 | 7/1980 |
| WO | WO 93/13707 | 7/1993 |
| WO | WO 95/33983 | 12/1995 |
| WO | WO 99/45352 | 9/1999 |
| WO | WO 2008/034010 | 3/2008 |
| WO | WO 2009/054800 | 4/2009 |
| WO | WO 2010/030882 | 3/2010 |
| WO | WO 2010/105356 | 9/2010 |
| WO | WO 2011/027282 | 3/2011 |
| WO | WO 2011/088572 | 7/2011 |
| WO | WO 2011/090744 | 7/2011 |
| WO | WO 2011/123689 | 10/2011 |
| WO | WO 2012/000798 | 1/2012 |
| WO | WO 2012/061935 | 5/2012 |
| WO | WO 2012/090210 | 7/2012 |
| WO | WO 2013/028613 | 2/2013 |
| WO | WO 2013/033489 | 3/2013 |
| WO | WO 2014/025255 | 2/2014 |
| WO | WO 2015/109339 | 7/2015 |
| WO | WO 2017/013020 | 1/2017 |
| WO | WO 2017/049392 | 3/2017 |

OTHER PUBLICATIONS

European Search Report issued in EP 11 83 9309, dated Mar. 20, 2014, in 1 page.

International Search Report issued in PCT Application No. PCT/CA2011/001257, dated Mar. 6, 2012, in 4 pages.

* cited by examiner

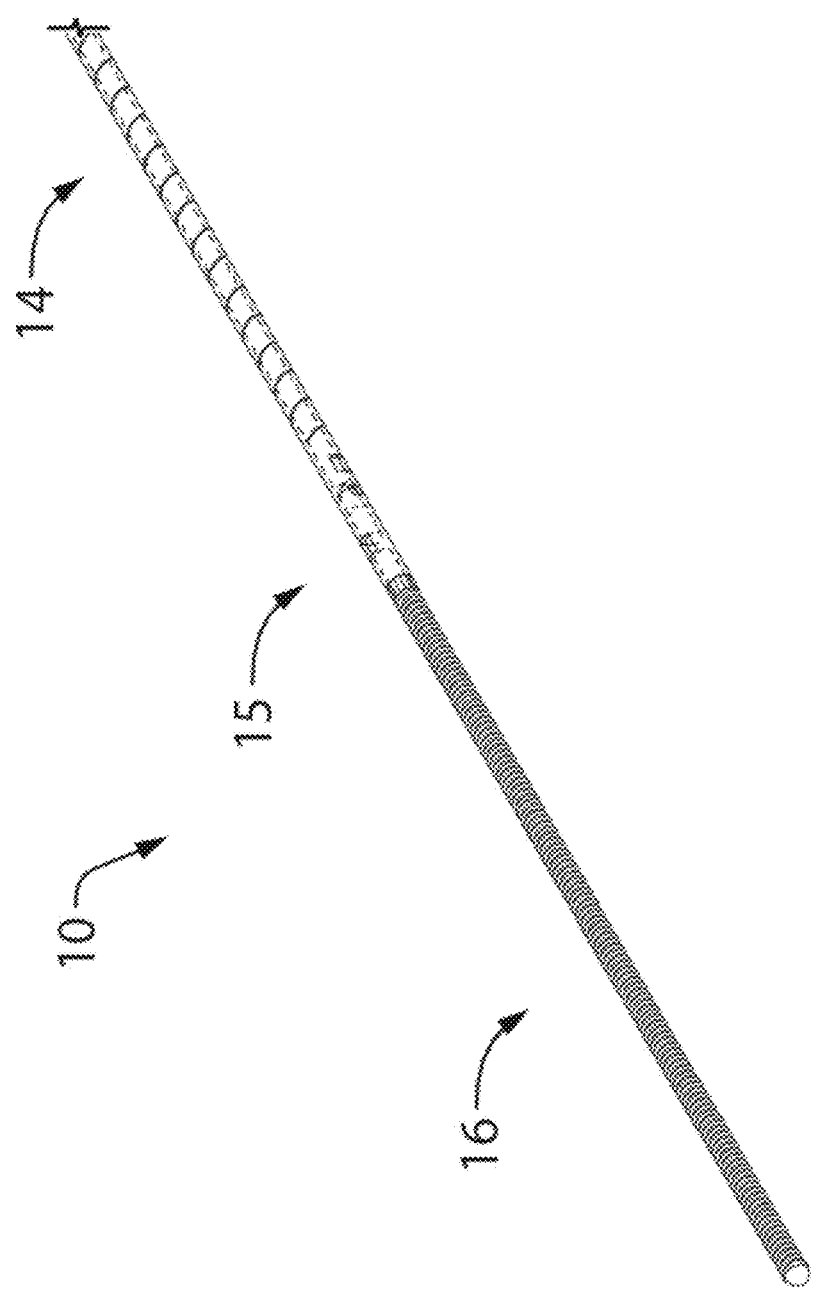

GUIDEWIRE WITH INTERNAL PRESSURE SENSOR

CROSS-REFERENCE TO RELATED APPLICATIONS

This application is a continuation application of U.S. patent application Ser. No. 16/128,957, filed on Sep. 12, 2018, which is a continuation application of U.S. patent application Ser. No. 15/918,677, filed on Mar. 12, 2018, which is a continuation application of U.S. patent application Ser. No. 14/138,392 filed on Dec. 23, 2013, which is a continuation of U.S. patent application Ser. No. 14/030,425 filed Sep. 18, 2013, which is a continuation of U.S. patent application Ser. No. 13/389,319 filed Feb. 7, 2012, which is the US national phase application of PCT/CA2011/001257, filed Nov. 9, 2011, and entitled "GUIDEWIRE WITH INTERNAL PRESSURE SENSOR", which claims priority of U.S. Provisional Application Ser. No. 61/411,722, filed on Nov. 9, 2010, the contents of which are hereby incorporated herein by reference in their entirety.

BACKGROUND

(a) Field

The subject matter disclosed generally relates to guidewires for catheter use. More particularly, it relates to pressure guidewire technology.

(b) Related Prior Art

Conventional Guidewires

Conventional guidewires are made using solid rods. They may be made using a combination of different materials such as hard tempered stainless steel and nitinol. Stainless steel provides good pushability and torquability, and is relatively cheap, while the nitinol provides good yield strength, i.e., does not permanently deform. Nitinol is nickel/titanium alloy having superelastic properties as known by those skilled in the art. One consideration in designing guidewires is that welding nitinol to stainless steel is extremely challenging.

Typical guidewires comprise three main parts as described below.

The first part is the proximal section. For coronary use, the proximal section, i.e., the length prior to the last 25 to 40 cm, is made typically of 0.014" outside diameter (OD) stainless steel. Nitinol is not preferred in this section because it does not provide a good pushability and torquability and it is fairly expensive. This section always resides in the catheter guide, hence not directly into the blood vessel. In use, a portion of this section is outside the patient's body and is controlled by the person using the guidewire. The typical length of the proximal section is 140 cm or longer.

The second part is the middle section. The middle section is the following 25 to 40 cm of flexible wire, before the tip portion, i.e., the third portion extending further over another 3 to 4 cm. The middle section is the section that navigates within the coronary arteries. Guidewires may use a nitinol wire of about 0.0095" OD over this section. In order to improve the navigability within the vessel, i.e., having the ability to be threaded through sharp corners within vessels, the distal 1 to 3 cm portion of the middle section, may be slightly tapered, the outside diameter being reduced roughly from 0.0095" to 0.007". This taper allows the guidewire to bend with a circular shape, as opposed to a parabolic shape in the case where the outside diameter is uniform. This section can be bent quite seriously when navigating into the vessels and hence, shape retaining is a desirable feature, although not a necessary one.

The third part is the tip section. The tip is the last 3 to 4 cm of the guidewire. It is made with a very thin tapered, or shaped otherwise, spring tempered or hardened stainless steel core wire. The core wire is surrounded by tungsten, platinum, palladium or another wire winding providing smooth radiopaque tip. Tip section can be pre-shaped prior to use by physician to ease the navigation in any given circumstance.

Guidewire features are:

Good trackability: Guidewire can be threaded through tortuous vessels;

Good pushability: Guidewire can be pushed through tortuous vessels and through stenosis;

Good torque: Guidewire can be smoothly rotated to orient the tip within the vessel;

Soft tip: Guidewire is atraumatic for vessels; and

Good support: A balloon catheter can be slid over the guidewire without the guidewire prolapsing or kinking.

Pressure Guidewire

A pressure guidewire is one that includes a tip pressure sensor. Trade-offs are necessary to route the sensor lead wire(s) through the guidewire, resulting in sub-optimal mechanical design. Existing pressure guidewires typically comprises four main parts as described below.

The first part is the proximal section. The proximal section is made with a stainless steel hypotube (aka the proximal tube) having typical OD of 0.014". There are three sensor lead wires that are routed through the proximal tube to connect to tip sensor.

The second part is the middle section. A solid core is welded to the proximal section on one end, and to a sensor housing on the other end. This solid rod is typically 27 cm long. The three wires of typical piezo-resistive sensor run through the proximal tube and on the wall of the core along the 27 cm. The three wires are finally directed within the sensor housing (described below) to be connected to the sensor.

The solid core and three wire assembly are protected either by providing a polyimide tube covering the assembly, by providing a spiral wound wire or other method for the assembly. The foregoing covering method provides minimal mechanical benefit and therefore they are used mostly as a protective sheath.

The third part of the pressure guidewire is the sensor housing. The sensor housing is made with a hypotube with internal diameter (ID) accommodating the tip sensor and an OD that is the continuity of the proximal section OD. An opening is provided to the sensor housing to let blood communicate with tip sensor.

The fourth part of the pressure guidewire is the tip section. The tip section is provided at the end of the sensor housing. A conventional tip section can be used as there is no wire to be passed therethrough.

The critical part of above described pressure guidewires is the middle section (second part above). Wall thickness of polyimide or wire winding added to the size of the sensor lead wires that runs along the solid core compromise the use of optimal solid core. More specifically, the solid core is usually too thin for delivering adequate pushability and torquability on one hand, and adequate support for a balloon catheter on another hand.

SUMMARY

The device described herein optimizes the mechanical performance; mode specifically it improves the pushability, torquability, trackability and catheter support in the case of a pressure guidewire.

As a first basic consideration, mechanical performance of prior pressure guidewires can be improved if instead of routing the sensor leads through a region toward the perimeter of the guidewire, therefore relying on a thin solid core for the transfer of torque, the sensor leads are routed through the center. It is known that contribution to torque transfer from the central part of a rod is lower than the contribution from the periphery of the same and therefore, it is optimal sacrificing the central portion rather than its periphery. This way, the torque per available surface area is maximized.

The size of the distal portion of such a hypotube, the portion that navigates within the coronaries, that delivers optimal flexibility and torquability may however be susceptible to kinking, as it would have to be a fairly thin hypotube if made of stainless steel. It is then useful to provide a mechanism that protects this otherwise vulnerable section against the risks of kinking. Protection against kinking is very suitably provided by the continuity of a proximal hypotube extending over, but being cut with a spiral or other pattern.

The use of a nitinol tube, instead of stainless steel tube, within the middle section of the guidewire would reduce the risk of kinking. The joining of nitinol is however a challenging process and there is a risk of leaving any of the guidewire distal parts within the blood vessel. It is then also desirable to provide a safety mechanism for retaining any of the distal parts of guidewire in case the joining of nitinol was to fail.

The presence of a continuous shaft from the very proximal end of the guidewire, up and after the sensor housing provides safety features critical for medical devices.

Manufacturability is another consideration, where the guidewire device needs to be produced in large quantity at the lowest possible cost. Having a minimal amount of parts surely contributes minimizing the manufacturing cost, as well as ease of assembly.

According to an embodiment, there is provided a pressure guidewire having a longitudinal axis comprising: a shaft tube having a proximal section and a sensor housing having a distal end; a fiber optic pressure sensor assembly embedded in the sensor housing and comprising a pressure sensor and an optical fiber extending within the sensor housing, the pressure sensor adapted to measure a pressure of a fluid which is substantially applied in an axis collinear with the longitudinal axis of the guidewire; and a band to support the fiber optic pressure sensor assembly, the band being embedded inside the sensor housing and fixed to the fiber optic pressure sensor assembly for holding the pressure sensor inside the sensor housing.

According to an aspect, the pressure guidewire further comprises a tip portion extending distally relative to the sensor housing, the tip portion having a proximal end attached to the distal end of the sensor housing, the tip portion being the most distal portion of the pressure guidewire.

According to an aspect, the shaft tube comprises a proximal section, the proximal section and the sensor housing being the continuity of the same shaft tube.

According to an aspect, the pressure guidewire further comprises a middle section extending further distally relative to the proximal section, the middle section being cut according to a cut pattern thereby resulting in greater flexibility in the middle section than in the proximal section.

According to an aspect, the pressure guidewire further comprises an inner hypotube and a window giving access to the inner hypotube for welding, soldering or bonding the inner hypotube within the middle section of the pressure guidewire.

According to an aspect, the pressure guidewire further comprises a small piece of material in contact with a wall of the inner hypotube and protruding within the window, the small piece of material being welded to the inner hypotube.

According to an aspect, the middle section has two ends and comprises two windows, each one of the two windows located at a respective one of the two ends of the middle section and thereby providing two areas for welding, soldering or bonding the inner hypotube within the middle section of the shaft tube.

According to an aspect, the sensor housing defines a cavity, inside the sensor housing, which is distal relative to the pressure sensor and delimited at a proximal end thereof by the pressure sensor.

According to an aspect, the sensor housing comprises an opening for letting a fluid penetrate in the cavity and contact the pressure sensor for measuring a pressure of the fluid.

According to an aspect, the pressure sensor comprises a diaphragm sensitive to a pressure of a fluid.

According to an aspect, the diaphragm substantially defines a plane which is perpendicular to the longitudinal axis.

According to an aspect, the cavity is delimited at a proximal end thereof by the diaphragm of the pressure sensor.

According to an aspect, the opening comprises two apertures in the sensor housing, thereby allowing the fluid to flow through the opening.

According to an aspect, the band is a radio opaque marker band.

According to an aspect, the band is a non-radio opaque marker band.

According to an aspect, the band is spaced apart from the pressure sensor.

According to an aspect, the band is disposed immediately proximal to the pressure sensor.

According to an aspect, the band is bonded to the sensor housing.

According to an aspect, the band is bonded by an adhesive.

According to an aspect, the band is bonded by an adhesive to the fiber optic pressure sensor assembly.

According to an aspect, the band is bonded to the optical fiber of the fiber optic pressure sensor assembly.

According to an aspect, the band is secured to the sensor housing by a weld.

According to an aspect, the band is secured within the sensor housing by soldering.

According to an embodiment, there is provided a sensor housing of a pressure guidewire having a distal end to be inserted in a patient's vessels, comprising: a fiber optic pressure sensor assembly embedded in a sensor housing and comprising a pressure sensor and an optical fiber extending within the sensor housing; and a band fixed to both the sensor housing and to the fiber optic pressure sensor assembly for holding the pressure sensor inside the sensor housing, wherein the sensor housing defines a cavity for receiving a fluid, inside the sensor housing, which is distal relative to the pressure sensor and delimited at a proximal end thereof by the pressure sensor.

According to an aspect the sensor housing further comprises an opening for letting the fluid penetrate in the cavity and contact the pressure sensor for measuring a pressure of the fluid.

According to an aspect, the pressure sensor comprises a diaphragm sensitive to a pressure of a fluid.

According to an aspect, the cavity is delimited at a proximal end thereof by the diaphragm of the pressure sensor.

According to an aspect, the opening comprises two apertures in the sensor housing, thereby allowing the fluid to flow through the opening.

According to an aspect, the band is a radio opaque marker band.

According to an aspect, the band is a non-radio opaque marker bad.

According to an aspect, the band is spaced apart from the pressure sensor.

According to an aspect, the band is disposed immediately proximal to the pressure sensor.

According to an aspect, the band is bonded to the sensor housing.

According to an aspect, the band is bonded by an adhesive.

According to an aspect, the band is bonded by an adhesive to the fiber optic pressure sensor assembly.

According to an aspect, the band is bonded to the optical fiber of the fiber optic pressure sensor assembly.

According to an aspect, the band is secured to the sensor housing by a weld.

According to an aspect, the band is secured within the sensor housing by soldering.

As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 5. is a perspective view showing the tip section of pressure guidewire of FIG. 1, FIGS. 6A and 6B are perspective views showing the small piece fitted to join or interlock nitinol inner tube to shaft tube.

It will be noted that throughout the appended drawings, like features are identified by like reference numerals.

DETAILED DESCRIPTION

Figure 1:
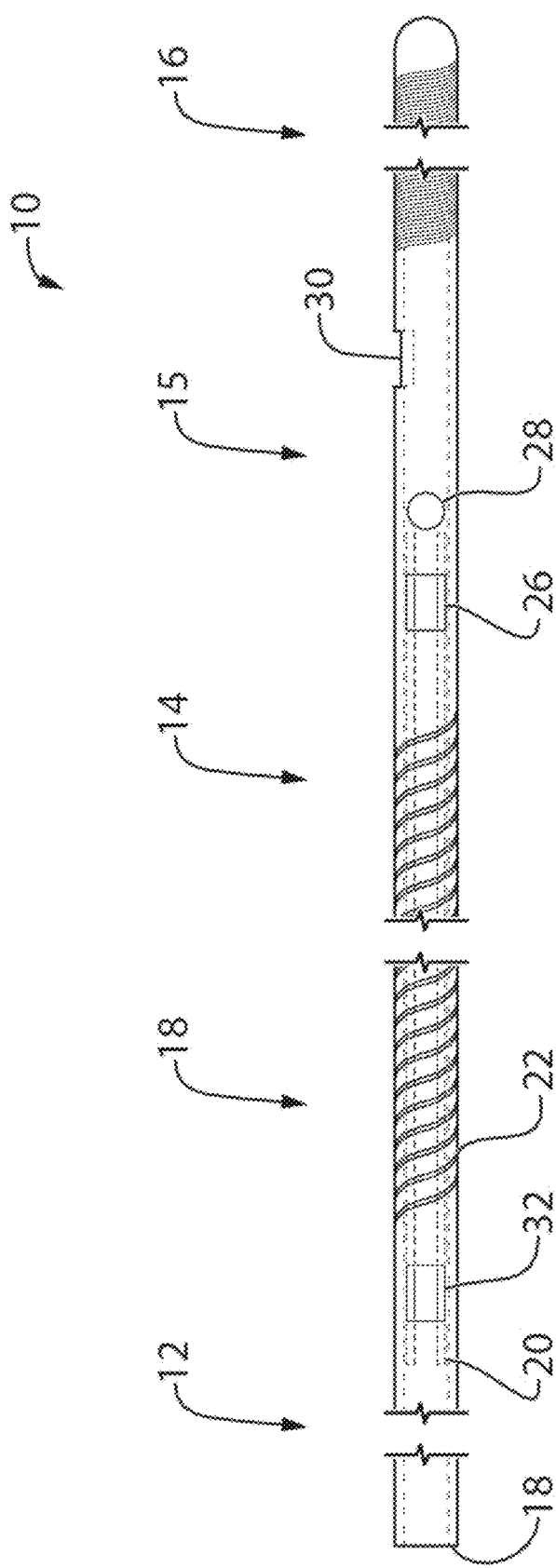
FIG. 1 is a schematic diagram which illustrates partial side view of an embodiment of the pressure guidewire.

Referring now to the drawings, and more particularly to FIGS. 1 to 6, there is shown an embodiment of a pressure guidewire 10.

The general design for the pressure guidewire shown in FIG. 1 herein, although it is made of fewer parts than prior art pressure guidewires, it is also made of same four sections, namely, the proximal section 12, the middle section 14, the sensor housing section 15 and the tip section 16. Although, as it will become clear hereinafter, the first three sections 12, 14 and 15 are to some extent made of the continuity of the same shaft tube 18, the above sections of shaft tube 18 may also be called herein after as proximal section 12, middle section 14 and sensor housing section 15.

According to an embodiment, the proximal section 12 is made of a stainless steel hypotube, with an OD of about 0.014" and by way of non limiting example with an ID of about 0.009". The proximal section is used to push other more distal sections of the pressure guidewire within the vasculature. The proximal section resides within the guiding catheter at one end, with the other end exiting the patient through the introducer (not shown), therefore allowing the physician to remotely control the pressure guidewire within the blood vessel, such as pushing and torquing the wire. According to an embodiment, the length of the sensor housing 15 is in a range between 1 mm to 3.5 mm. According to an embodiment, the length of the sensor housing 15 is 2.5 mm.

The middle section is the one that faces the most challenging trade-offs. The middle section 14 must not damage the vessel and hence it must be fairly flexible. It must however transmit the torque for better navigability, be stiff enough to deliver a good pushability and provide a good support for an angioplasty balloon. The middle section can be made by extending the proximal section 12 further, but it would be too stiff to navigate within the vessels. On the other hand, the middle section 14 can be softened by cutting the tube as a spiral or other cutting patterns as known by those skilled in the art. Those skilled in the art also know that such cut patterns are achieved using laser, etching and other processes. Spiral cutting the tube would result in a very soft section whether the pitch is high or low, and would not deliver any of the required tensile force and torque response. Other non continuous cut patterns can provide adequate tensile force, but the stiffness is controlled by adjusting the pitch and cut pattern. It is however difficult to provide a smooth and continuous variation of stiffness. There is also a critical safety challenges when torquing such a cut patterned guidewire as the torque induced stresses are concentrated in narrow cut regions of the guidewire, hence potentially provoking guidewire failure.

Using the device described hereinafter it is possible to control safely the mechanical performance of the middle section 14 by way of a) extending the proximal section 12 further; b) cut this extended section to soften it; and c) combining this cut section with an additional inner hypotube 20 overlapping the whole cut region of middle section 14, the inner hypotube geometry being chosen such that the desired mechanical characteristics are achieved. The middle section 14 is the continuity of the proximal section 12, where the portion corresponding to the 27 cm middle section 14 of the shaft tube 18 is cut, such as a spiral cut shaft tubing 22 according to one embodiment. The spiral cut section of the shaft tubing 22 does not provide any significant tensile strength nor does it provide significant bending or torque strength.

The inner hypotube 20 is inserted within the shaft tube 18 such that it overlaps the middle section 14, where the tubing is cut. The outside diameter (OD) of the inner hypotube 20 fits the inside diameter (ID) of shaft tube 18 and can be of 0.009" in an embodiment. The ID of the inner hypotube 20 must accommodates the sensor lead wire, or communication means (not shown in FIG. 1), as is the case of the ID of the shaft tube 18. Sensor communication means can be made fairly small, especially if optical fiber is used, so the inner hypotube 20 can provide the desired mechanical properties. By way of another non-limiting example, inner hypotube ID can be of 0.005".

One problem if such an inner hypotube 20 was used alone is that it may not provide adequate resistance against kinking. In the absence of the spiral cut shaft tubing overlay, or other cut pattern, a more conventional design would involve the addition of an elastomer coating to bring the outer diameter of the inner tube to a similar diameter as that of the shaft tube 18 (i.e., the stainless steel hypotube). However, this would not improve the resistance against kinking, which is a safety consideration.

Another safety issue is the risk of leaving parts inside the patient as a result of joint failure between inner tube and proximal tube or sensor housing. In case of a joint failure in more conventional designs, such as the one proposed in U.S. Pat. No. 5,085,223 and Patent appl. No. US2010/0318000, the risk of leaving the distal parts of the guidewire within the blood vessel in case of joint failure is quite important. The proposed design mitigates this risk by providing a spiral cut pattern external tube that covers an inner hypotube, the inner tube providing most of the mechanical characteristics of the middle section. In case of joint failure resulting from applying a pulling force too strongly, the spiral cut tube will collapse over and grip the inner hypotube 20, thereby bringing along the distal portion of the guidewire.

The spiral cut shaft tubing 22, when provided with an inner hypotube 20, delivers the desired mechanical characteristics. Stiffness (flexibility), torque transfer, pushability and support are provided by the inner hypotube 20. Inner hypotube 20 dimensions are easily adapted to provide optimal mechanical performance. On the other hand, kink resistance, distal parts safety retainer, and guidewire outside diameter continuity are provided by the spiral cut shaft tubing 22. It is worth mentioning that kink resistance provided by the spiral cut section is useful mostly in cases where the inner hypotube is not nitinol, e.g., it is useful when inner hypotube is stainless steel.

Figure 4:
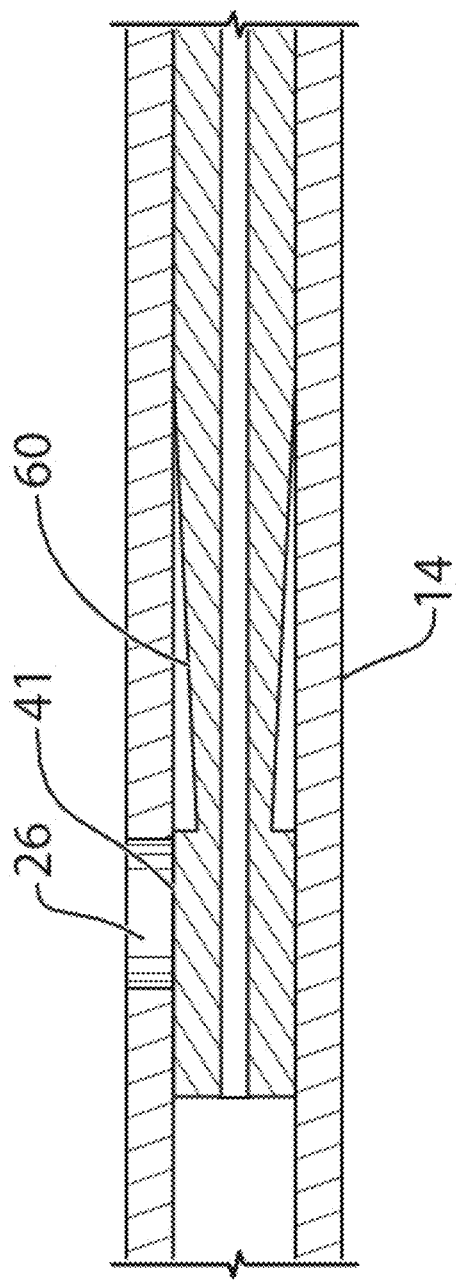
FIG. 4 is a schematic showing the profiling, in part, of the distal end of inner tube of the pressure guidewire of FIG. 1.

As shown by FIG. 4, it is also desirable to shape the outside diameter of the inner tube, especially over the last 1 to 3 cm, in order to further improve trackability. In this case, the external diameter of the distal portion of the inner hypotube 20 can be slightly grinded to taper its outer diameter 40 and hence, optimizing mechanical response.

The very end 41 of the inner hypotube 20, the portion that fits within the sensor housing section, should be enlarged, e.g., to the same diameter as its proximal section, so as to assure a good joint with the internal wall of the sensor housing section 15 (see FIGS. 1, 5 and 6). The very end 41 of the inner hypotube being enlarged assures a better joint for at least two reasons. One is that the gap between the inner hypotube and the internal surface of the sensor housing is minimized, which in turns optimizes the shear strength of the adhesive or soldering in between the sensor housing internal diameter and outside diameter of the very end 41 of inner hypotube. Another important reason is that an enlarged portion will have a much lower internal stress. When using nitinol, the risk of reaching a stress level corresponding to the first plateau of nitinol stress to strain curve as known by those skilled in the art, is much lower. When such first plateau is reached, the strain induced within a nitinol tubing is increasing dramatically, which may provoke a delamination of the adhesive or soldering, which in turn may cause the failure of the joint.

Figure 2:
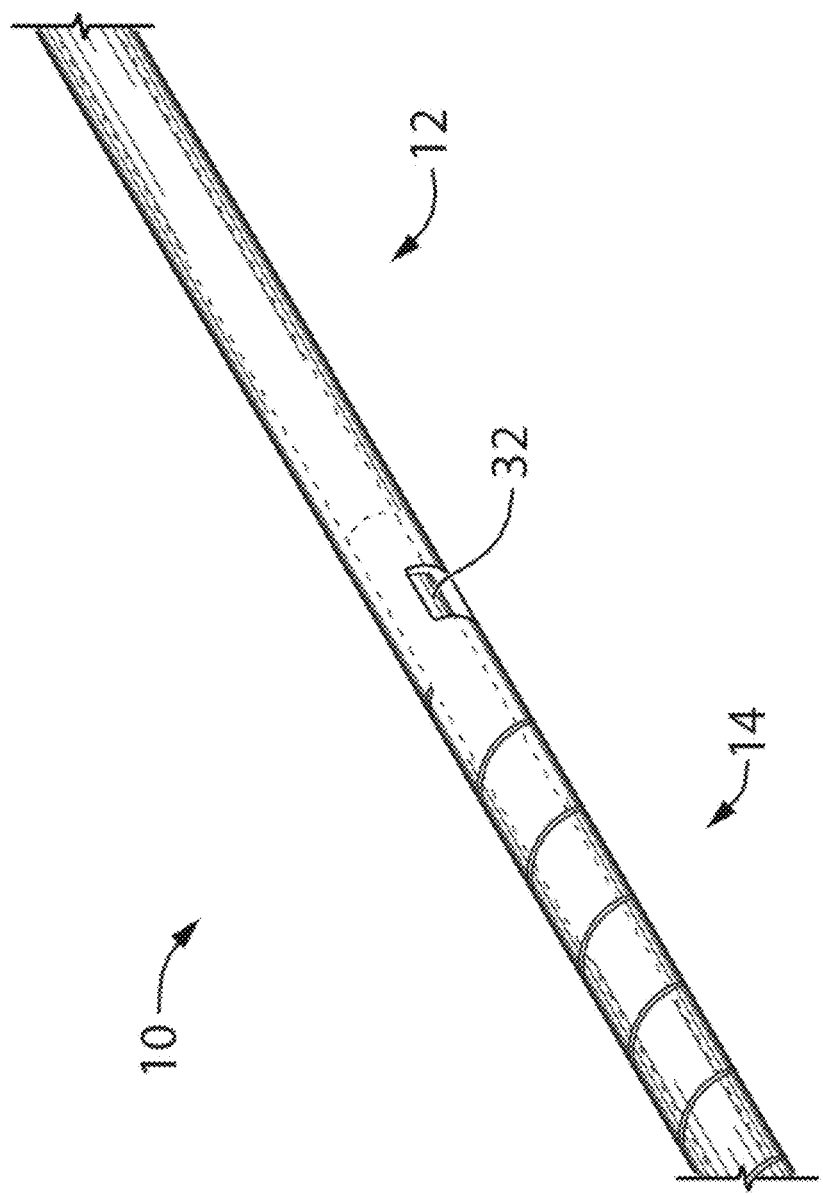
FIG. 2 is a partial perspective view showing the interfacing portion between the proximal and middle sections of pressure guidewire of FIG. 1.
Figure 3:
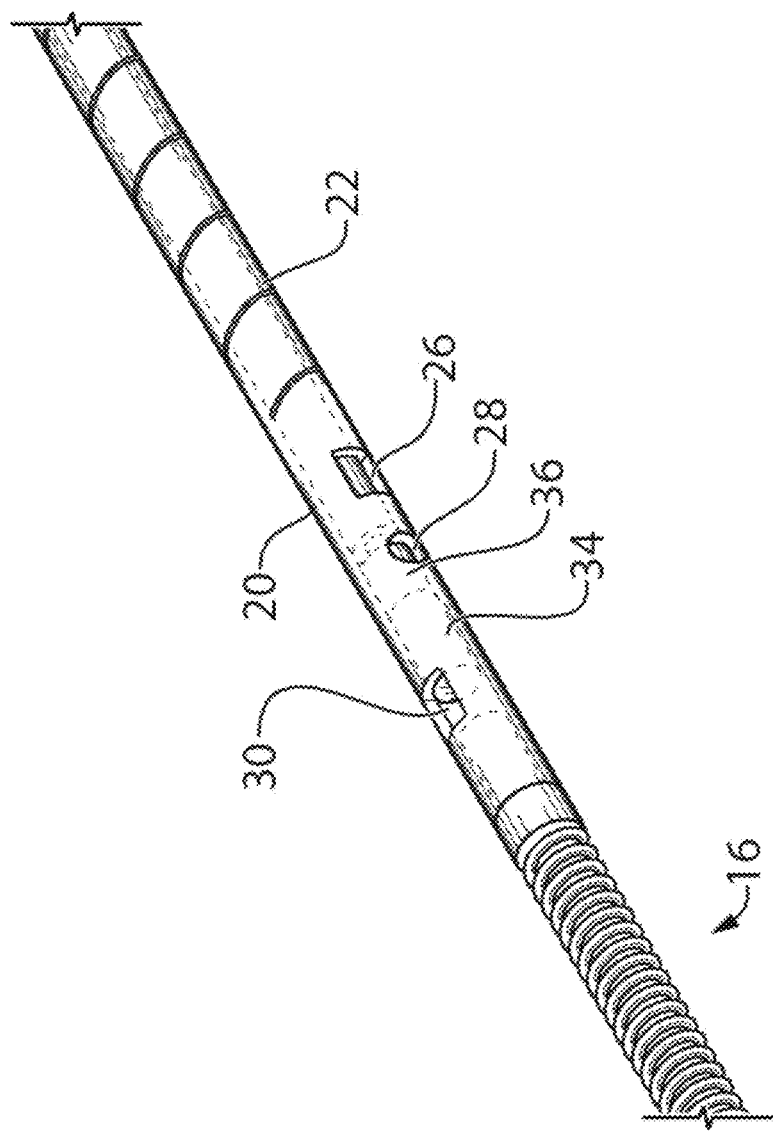
FIG. 3 is a partial perspective view showing the interfacing portion between the middle and sensor housing sections of the pressure guidewire of FIG. 1.

One method of joining the inner hypotube 20 to the ends of middle section 14 of shaft tube 18 is shown in FIG. 2. A window 32 is provided through the wall of the shaft tube 18, where the inner hypotube 20 is to be welded. The inner hypotube 20 is slid past the window and welded to the middle section 14 using a laser beam or other suitable welding or joining means. The laser beam melts and joins together the edges of the window 32 to the inner hypotube 20 and therefore, secures the two parts together. It is also possible to use the same window 32 to apply adhesive at the joint between the inner and outer tubes. It is also possible to weld the tubes together without such window by heating the outer surface of the outer tube such that it welds to inner tube. Such heat can be generated using a laser, an electron beam or another heat source.

Similar methods apply for joining the inner hypotube 20 to the other end of middle section 14, where another window 26 (FIG. 3) is provided at the distal end of middle section 14 of shaft tube 18. According to an embodiment, the length of windows 32 and 26 is in a range between 0.2 mm to 0.5 mm. According to an embodiment, the length of windows 32 and 26 is 0.3 mm. Both ends of inner hypotube 20 extend a little further past the position of windows 26 and 32.

Without the presence of an inner hypotube 20 within the cut middle section 14, blood may leak inside the shaft tube 18, which constitutes a fairly large volume, which in turn may cause biocompatibility issues. The presence of the inner hypotube 20 seals off the inside of the shaft tube 18 where it is cut.

The sensor housing section 15 is made of the very last 2 to 3 mm of the shaft tube 18. The spiral cut, or other cut patterns, stops some 2 to 3 mm before the end of the shaft tube 18, where the sensor 34 (see FIG. 3) is to be fitted. A sensor joining window 28 is provided to bond or to fix the sensor 34 within the sensor housing section 15. Blood pressure is applied to sensor 34 via opening 30. In the present description, sensor 34 comprises a pressure sensor. According to an embodiment, the length of the opening 30 is in a range between 0.2 mm to 0.5 mm. According to an embodiment, the length of the opening 30 is 0.3 mm. According to an embodiment, the diameter of the sensor joining window 28 is in a range between 0.1 mm to 0.3 mm. According to an embodiment, the diameter of the sensor joining window 28 is 0.2 mm. According to an embodiment, the pressure sensor comprises an optical pressure sensor.

A radiopaque marker band 36 may be located in the sensor housing section 15 to help in localizing the pressure guidewire in the vessels. The marker band, or otherwise similar non radiopaque band, main purpose is however to allow easy assembly of the sensor within the sensor housing. It is indeed preferable to avoid the application of hard adhesive directly on sensor head. The marker band 36 can be bonded to the pressure sensor communication means (e.g., optical fiber) as a pre-assembly in an environment allowing the control of adhesive flow. The sensor 34 is secured within pressure guidewire by bonding the marker band 36, or other non radiopaque band, to the sensor housing section 15 using sensor joining window 28.

A tip section 16 (FIG. 5) is provided at the end of the sensor housing section 15. A conventional atraumatic tip section 16 shown in FIG. 3 can be used as there is no sensor lead wire to be passed therethrough.

Having similar materials for shaft tube 18 and inner hypotube 20, such as stainless steel, makes the above welding process fairly simple and reliable. It may however be desirable to use dissimilar materials that cannot easily be welded together. For example, it is desirable to use shaft tube 18 made of stainless steel for providing a good pushability, while it is also desirable to use nitinol for the inner hypotube 20 for its superior yield strength and lower elastic modulus. It is well known by those skilled in the art that those two materials are not easily welded together, at least not without an intermediate material.

Figure 6A:
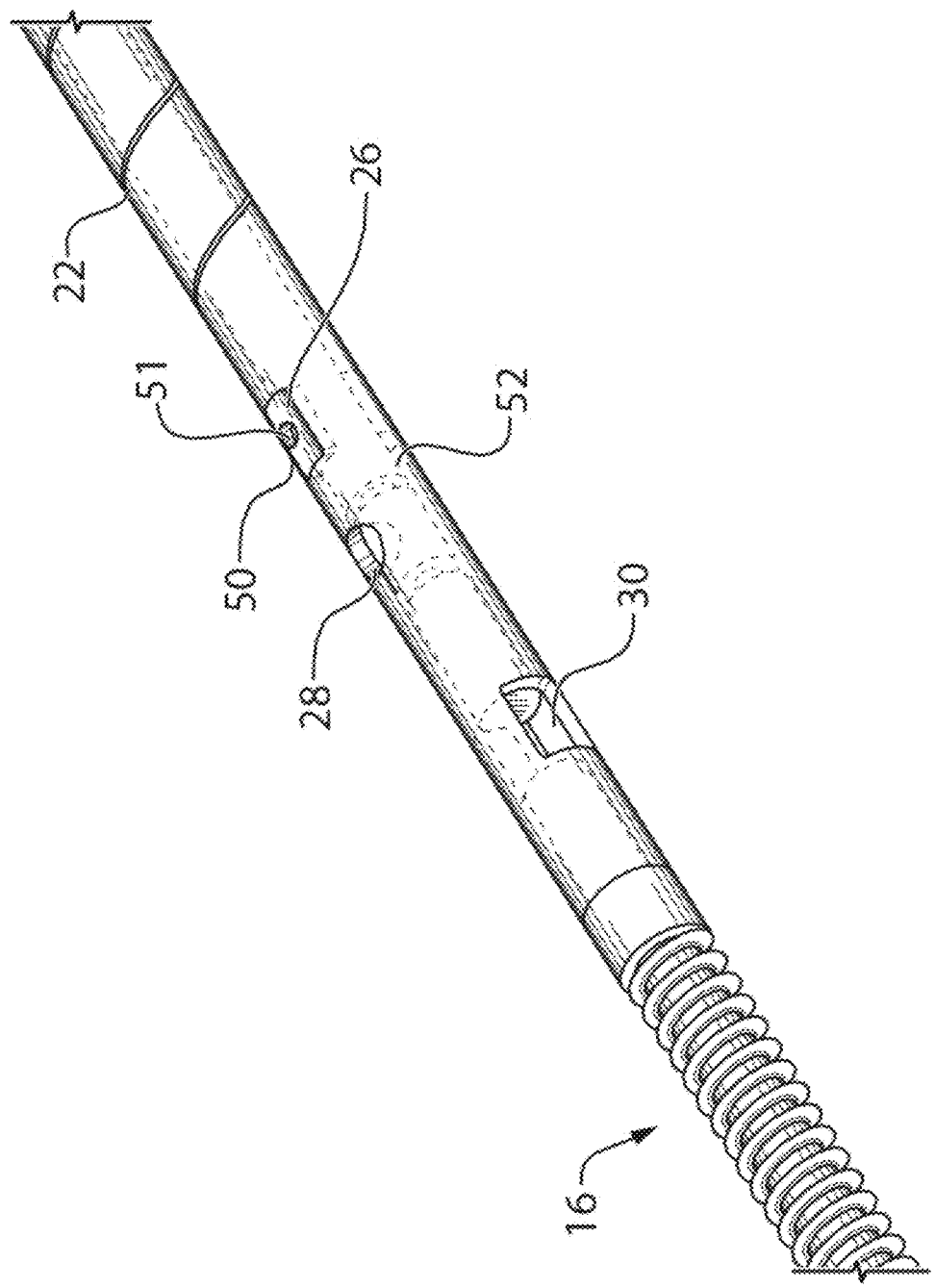
Figure 6B:
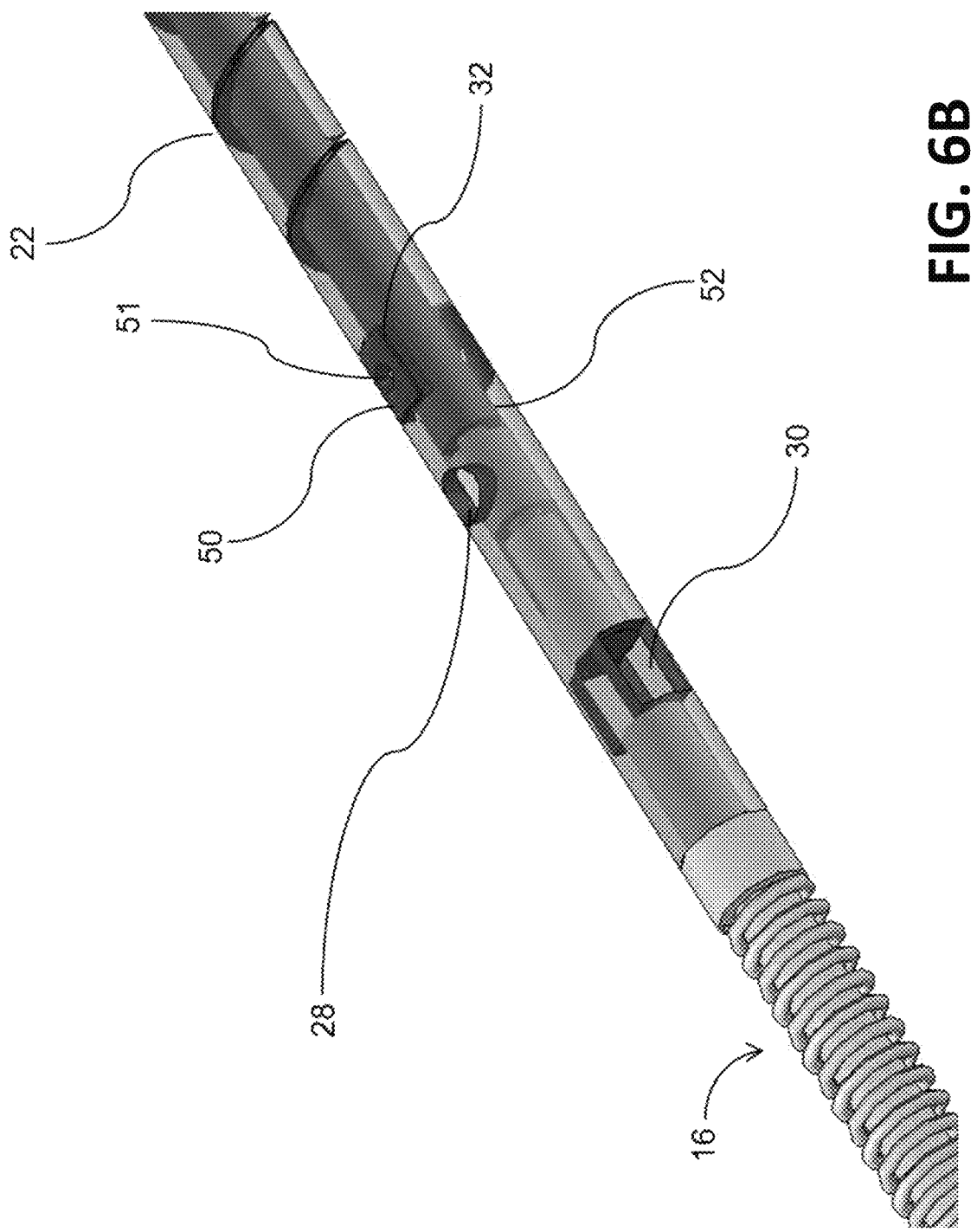

The present description also discloses a method for joining together those dissimilar materials. FIG. 6 shows one method of joining an inner hypotube made of nitinol to a stainless steel middle section 14 hypotube. The inner hypotube 52 is slid within the shaft tube 18 to overlap the cut section, and fed through past the windows 26 and 32 (only window 26 shown in FIGS. 6A and 6B). A small piece 50 of nitinol that fits in the windows is machined, inserted into the window 32 to get in contact with the inner hypotube 52 once in place, and laser welded to the inner hypotube 52, interlocking the two parts together. The small piece 50 then prevents the inner hypotube 52 from sliding within shaft tube 18. A small amount of adhesive can also be added to eliminate any movement of the small piece 50 relative to shaft tube windows 28 and 32.

Another method of joining the above inner hypotube 52 to stainless steel shaft tube 18 is to use an intermediate material, for example nickel, that can be welded to both nitinol and stainless steel. A small piece 50 made of nickel can be laser welded to inner hypotube 52 first. A small hole in the center 51 can be provided to promote heat transfer to inner hypotube 52. The inner hypotube 52 is then interlocked to proximal section 12 as described above. The edges of the small piece 50 of nickel can then be laser welded to shaft tube 18. In this case, no direct welding of nitinol to stainless steel occurs and therefore, no brittle interface is created.

Another method involves the use of adhesive to bond the nitinol inner hypotube 20 to the stainless steel shaft tube 18. The same parts can also be soldered together and by any other methods known by those skilled in the art.

It can be appreciated that the design is made with one single uniform part, from proximal section 12 to the sensor housing section 15, and therefore the guidewire 10 is very smooth with minimum mechanical steps.

The manufacturability of this design is quite easy and very efficient as the number of parts is minimized.

The mechanical properties can be optimized by varying the respective wall thicknesses of inner hypotube 20 and shaft tube 18.

The pitch of the spiral cut or other laser cut pattern can be varied ideally from a larger pitch to a shorter one when approaching the sensor housing section 15. Sharp turns are expected to arise in the region of the sensor housing section 15, near the tip of the guidewire 10 and therefore, it would be best if the pitch of the laser cut pattern was reduced near the sensor housing section 15 to allow a smoother bending of the cut shaft tubing 22.

For improved safety, the spiral cut pattern provides a retainer for distal portions of guidewire. Risks of leaving parts inside patient body are therefore minimized.

There will be an optical connector (not shown) at the very proximal end of the guidewire 10.

As known by those skilled in the art, above described pressure guidewire can be coated with different material such as Teflon or hydrophilic coating so as to reduce friction against wall of vessels and/or guiding catheter.

Figure 7:
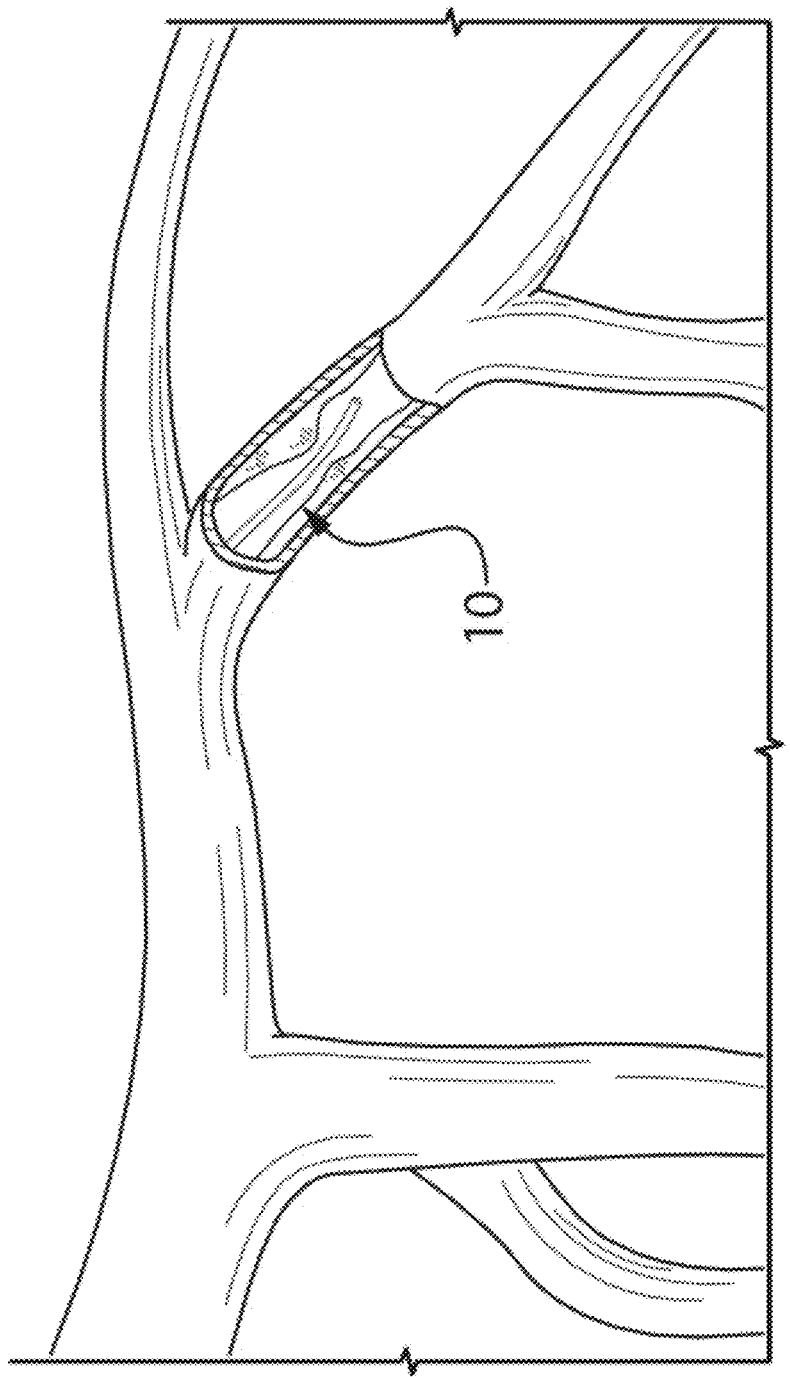
FIG. 7 is a schematic diagram showing blood vessels with a cut-out portion in which a pressure guidewire is inserted.

Now referring to FIG. 7, there is shown blood vessels with a cut-out portion in which a pressure guidewire 10 is inserted.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A pressure guidewire comprising:
   a sensor housing;
   a sensor assembly embedded in the sensor housing and comprising a pressure sensor; and
   a band to support the pressure sensor assembly, the band being embedded inside the sensor housing and fixed to the pressure sensor assembly for holding the pressure sensor inside the sensor housing.

2. The pressure guidewire of claim 1, wherein the pressure guidewire has a longitudinal axis, the pressure sensor adapted to measure a pressure of a fluid which is substantially applied in an axis collinear with the longitudinal axis of the guidewire.

3. The pressure guidewire of claim 1, wherein the sensor housing has a distal end, further comprising a tip portion extending distally relative to the sensor housing, the tip portion having a proximal end attached to the distal end of the sensor housing, the tip portion being the most distal portion of the pressure guidewire.

4. The pressure guidewire of claim 1, wherein the pressure guidewire comprises a shaft tube comprising the sensor housing, the shaft tube comprising a proximal section, the proximal section and the sensor housing being the continuity of the same shaft tube.

5. The pressure guidewire of claim 4, wherein the shaft tube further comprises:
   a proximal section to provide pushability to the pressure guidewire; and
   a middle section extending distally relative to the proximal section, the middle section comprising a cut pattern to provide greater flexibility in the middle section than the proximal section,
   wherein the sensor housing extends distally relative to the middle section.

6. The pressure guidewire of claim 5, further comprising an inner hypotube comprising a proximal end portion and a distal end portion, the inner hypotube positioned entirely radially inward of the shaft tube and within at least the middle section, the proximal end portion and the distal end portion of the inner hypotube being joined to the shaft tube.

7. The pressure guidewire of claim 6, further comprising a window giving access to the inner hypotube for welding, soldering or bonding the inner hypotube within the middle section of the pressure guidewire.

8. The pressure guidewire of claim 7, further comprising a small piece of material in contact with a wall of the inner hypotube and protruding within the window, the small piece of material being welded to the inner hypotube.

9. The pressure guidewire of claim 1, wherein the band is a radio opaque marker band.

10. The pressure guidewire of claim 1, wherein the band is spaced apart from the pressure sensor.

11. The pressure guidewire of claim 1, wherein the band is disposed immediately proximal to the pressure sensor.

12. The pressure guidewire of claim 1, wherein the band is bonded to the sensor housing.

13. The pressure guidewire of claim 12, wherein the band is bonded by an adhesive.

14. The pressure guidewire of claim 13, wherein the band is bonded by an adhesive to the pressure sensor assembly.

15. The pressure guidewire of claim 1, wherein the band is secured to the sensor housing by a weld.

16. The pressure guidewire of claim 1, wherein the band is secured within the sensor housing by soldering.

17. The pressure guidewire of claim 1, wherein the sensor housing defines a cavity, inside the sensor housing, which is distal relative to the pressure sensor and delimited at a proximal end thereof by the pressure sensor, the pressure sensor comprises a diaphragm sensitive to a pressure of a fluid within the cavity.

18. A sensor housing of a pressure guidewire having a distal end to be inserted in a patient's vessels, comprising:
   a fiber optic pressure sensor assembly embedded in a sensor housing and comprising a pressure sensor and an optical fiber extending within the sensor housing; and
   a band maintaining the fiber optic pressure sensor assembly in the sensor housing.

19. The sensor housing of claim 18, wherein the band is spaced apart from the pressure sensor.

20. The sensor housing of claim 18, wherein the band is disposed immediately proximal to the pressure sensor.

* * * * *